(12) United States Patent
Kabanov et al.

(10) Patent No.: US 6,656,459 B2
(45) Date of Patent: Dec. 2, 2003

(54) COMPOSITIONS OF NON-IONIC BLOCK COPOLYMERS TO TREAT AUTOIMMUNE AND INFLAMMATORY DISEASES, AND TO REDUCE GRAFT/IMPLANTATION, AND METHODS OF USE THEREOF

(75) Inventors: Alexander V. Kabanov, Omaha, NE (US); Pierre Lemieux, Longueuil (CA); Nadia Guerin, St. Therese (CA); Valery Alakhov, Montreal (CA)

(73) Assignee: Supratek Pharma Inc., Dorval (CA)

( * ) Notice: Subject to any disclaimer, the term of this patent is extended or adjusted under 35 U.S.C. 154(b) by 0 days.

(21) Appl. No.: 09/852,533

(22) Filed: May 10, 2001

(65) Prior Publication Data

US 2002/0028190 A1 Mar. 7, 2002

Related U.S. Application Data

(60) Provisional application No. 60/203,549, filed on May 12, 2000.

(51) Int. Cl.$^7$ .................. A61K 31/74; A61K 31/785; A61K 9/00
(52) U.S. Cl. ................. 424/78.03; 424/280.1; 424/400; 424/78.05; 424/78.18; 424/78.31
(58) Field of Search .................. 424/78.03, 280.1, 424/400, 78.05, 78.18, 78.31; 514/724, 772.4

(56) References Cited

U.S. PATENT DOCUMENTS

| | | | | | |
|---|---|---|---|---|---|
| 5,166,219 | A | * | 11/1992 | Katz | 514/724 |
| 5,824,322 | A | * | 10/1998 | Balasubramanian | 424/280.1 |
| 5,840,319 | A | * | 11/1998 | Alakhov et al. | 424/400 |
| 6,218,438 | B1 | * | 4/2001 | Alakhov et al. | 514/772.4 |

OTHER PUBLICATIONS

STN Registry Searches for F 127, L 61, Pluronic F 127 and Pluronic L 61, copies labeled 1–7.*

* cited by examiner

*Primary Examiner*—Thurman K. Page
*Assistant Examiner*—Blessing Fubara
(74) *Attorney, Agent, or Firm*—Mathews, Collins, Shepherd & McKay, P.A.

(57) ABSTRACT

Compositions comprising non-ionic block copolymers are useful for the treatment of autoimmune, inflammatory and proliferative diseases and for reducing graft/implantation rejection. The present invention also relates to methods of treating animals having various autoimmune, inflammatory and proliferative diseases. The present invention also relates to methods of reducing inflammation in an animal comprising administering the compositions of the invention. Also, the present invention relates to methods of reducing autoimmune responses and to methods of reducing graft/implantation rejection comprising administering the compositions of the inventions. A typical embodiment is a mixture of Pluronics F127 and L61.

15 Claims, No Drawings

COMPOSITIONS OF NON-IONIC BLOCK COPOLYMERS TO TREAT AUTOIMMUNE AND INFLAMMATORY DISEASES, AND TO REDUCE GRAFT/IMPLANTATION, AND METHODS OF USE THEREOF

CROSS REFERENCE TO RELATED APPLICATIONS

The benefit of Provisional Application No. 60/203549 filed May 12, 2000 is hereby claimed.

FIELD OF THE INVENTION

This invention relates to compositions comprising non-ionic block copolymers-useful for the treatment of various autoimmune, inflammatory and proliferative diseases and for reducing graft/implantation rejection. More specifically, the present invention relates to systemic anti-autoimmune, anti-inflammatory and anti-proliferative disease treatment using non-ionic block copolymers. The present invention also relates to methods of treating animals having various autoimmune, inflammatory and proliferative diseases. The present invention also relates to methods of reducing inflammation in an animal, in particular, a human, comprising administering the compositions of the invention. Further, the present invention relates to methods of reducing graft/implantation rejection comprising administering the compositions of the inventions.

BACKGROUND OF THE INVENTION

Autoimmune Diseases

Immunoregulatory abnormalities have been shown to exist in a wide variety of autoimmune and chronic inflammatory diseases, including but not limited to those specified in the examples, which are useful in a mammalian subject for the treatment and prevention of the resistance by transplantation of organs or tissue, graft-versus-host diseases brought about by medulla ossium transplantation; rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B.sub.4-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjogren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Addison's disease, ischemia-reperfusion injury of organs which occurs upon preservation, transplantation or ischemic disease, for example, thrombosis and cardiac infraction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_{.sub.4}$ release; Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmention of chemotherapeutic effect, preventing or treating activity of cytomegalovirus infection, HCMV infection, and antiinflammatory activity; and treatment of immunodepression or a disorder involving immunodepression, including AIDS, cancer, senile dementia, trauma, chronic bacterial infection, and certain central nervous system disorders.

Although the underlying pathogenesis of each of these conditions may be quite different, they have in common the appearance of a variety of autoantibodies and self-reactive lymphocytes. Such self-reactivity may be due in part to a loss of the homeostatic controls under which the normal immune system operates. Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Anti-inflammatory agents such as NSAID's act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

In the pathogenesis of most experimental autoimmune diseases, T lymphocytes play a crucial role in the initiation, whereas macrophages are essential in the effector phase. Several methods to elucidate the exact role macrophages play in different stages of autoimmune models in the rat. By using monoclonal antibodies an inventory has been made on the different macrophage subsets that are present in the infiltrates of the affected tissues. That macrophages play a decisive role in provoking the clinical signs has been shown by several macrophage elimination studies. The severe tissue damage caused by macrophages is brought about by the release of inflammatory mediators. Especially interference with the production or action of these products could provide new therapeutic means.

Pharmaceutical Agents for Autoimmune Disease Treatment

Conventional drugs used in the treatment of autoimmune diseases and graft/transplantation rejection, such as cyclosporin A, corticosteroids, azathioprine, polyclonal anti-lymphocyte globulins and monoclonal T cell antibodies are somewhat effective in electing an immunosuppressive response. However, their high toxicity profiles frequently limit their clinical benefit. Thus, the treatment of autoimmune diseases, graft/transplantation rejection and other pathologies requiring immunosuppression with agents having low-toxicity profiles remains a major clinical problem.

The use of monoclonal anti-IL2 receptor antibodies in combination with cyclosporin A has been reported. See, Diamantstein, T, et al., (1986) *Immunobiol.* 1:391–399; Kupiec-Weglinski, J. W., et al., (1988) *Transplant Proc.* 20:207–216 and Hancock, W. W., et al., (1990), *Transplantation* 49:416–421. The use of bromocriptine in combination with cyclosporin A (Carrier, M., et al., (1990), *Ann. Thorac. Surg.* 9:129–32) and thalidomide in combination with cyclosporin A (Tamura, F., et al., (1990) *Transplantation* 49:20–25) has also been reported.

Rheumatoid Arthritis and Anti-Arthritis Drugs

Among the autoimmune diseases, rheumatoid arthritis is medically termed as an inflammation of a joint or joints and is one of a number of diseases of the skeleton and body system. Arthritis arises from many causes, some well defined, some still unknown, and it is treated in many different ways. There are two common types of the disease, the first of which is inflammatory, and most commonly acknowledged as rheumatoid arthritis. The second type is non-inflammatory, and most commonly represented by degenerative joint disease, or wear and tear arthritis. Inflammatory arthritis is a disease that is not only related to the joints alone, but it is related to the entire body, in particular, the connective tissues of the body. Inflammatory arthritis is an autoimmune disease, where the body's immune system attacks own tissues and produces inflammation. Degenerative joint disease is a chronic joint disease, often occurring in more elderly individuals. In both cases many manifestations of the disease are similar. The joints, whether singly or in multiples, are affected. The joints may become swollen, warm, deformed, gnarled, and in many instances present grotesque deformities. In many cases it also affects the adjacent muscles and tendons, as well as other connective tissues of the body. The primary disease produces symptomatic swelling, pain and stiffness.

A variety of pharmaceutical agents have been developed for the treatment of arthritis, anywhere from non-steroidal anti-inflammatory drugs to cortisone. Many of these systemic drugs have dangerous side effects. Their dosage must be carefully prescribed and administered under controlled conditions and circumstances to avoid unpleasant and dangerous side effects.

Several topical agents (creams, ointments, liniments and the like) have been utilized for the relief of the pains and aches of arthritis. Most of these have provided a little, and only temporary, relief to the patients suffering from pain. Many combinations of varying ointments, creams, aqueous solutions, liniments and the like for the treatment of arthritis are known. The most efficacious of these contains as its active ingredient the vegetable products derived from the seed and pods of the capsicum plant, commonly known as red pepper. Capsicum-derived ointment is devised for external application to the affected area of the body by applying to the area adjacent to the muscle, joint or tendon and rubbing it into the skin. The active ingredient is capsaicin. With initial as well as persistent application, capsaicin is effective to relieve the aches and pains of various muscle or skeletal origin, such as arthritis, muscle strains, tendinitis, bursitis and soft tissue diseases.

Capsaicin is also effective to relieve the various neuropathic pains and dysesthesias caused by shingles, post herpetic neuralgia, and peripheral neuropathies. It is further commonly prescribed to reduce the pain of neuropathies produced by diabetes (burning pain, discomfort, often at night) and other diseases that are neuropathic in origin including the discomfort and odd sensations of shingles (post herpetic neuralgia, which can be extremely painful), as well as dysesthesias that can occur with thoracotomies and post surgical scars.

Unfortunately, although capsaicin is often the most effective agent available, the active ingredient in this drug is a potent skin irritant, producing a burning, uncomfortable sensation to the skin. Although prescribed frequently, it is used to only a limited extent due to this unpleasant side effect. The burning side effect has also discouraged the use of capsaicin to treat other types of discomfort, such as pruritus or itching. Pruritus or itching can be caused by many stimuli, such as poison ivy, hemorrhoids, or athlete's foot. The unpleasant side effects of capsaicin have discouraged its use to treat such types of discomfort. A capsaicin based pain reliever which does not irritate the skin or cause a burning discomfort would be extremely desirable and acceptable to patients and people in general who are experiencing the types of pain or discomfort outlined above.

Rheumatoid arthritis (RA) is a debilitating, chronic inflammatory disease affecting 1 to 2% of the world's population. This condition causes pain, swelling and destruction of multiple joints in the body and can also result in damage to other organs. People with advanced disease have a mortality rate greater than some forms of cancer and because of this, treatment regimes have shifted towards aggressive early drug therapy designed to reduce the probability of irreversible joint damage. Over the past decade there has been a radical change in the philosophy of treatment for rheumatoid arthritis. The traditional restrained approach to the introduction of second-line agents—drugs that work directly on improving the disease rather than targeting the symptoms—has been replaced by strong recommendations for early referral of suspected cases of rheumatoid arthritis and the initiation of second-line therapy within several months of the onset of symptoms. The treatments include the early initiation of DMARD (disease-modifying antirheumatic drug) therapy for any patient with an established diagnosis and ongoing symptoms. Anticancer drugs have become the first line of therapy for the vast majority of patients, with methotrexate (MTX) being the drug of choice for 60 to 70% of patients. Patients treated with MTX necessitate weekly treatments and see their conditions progress in 50% of the time. However, MTX is far from being the ideal drug for RA and further development of better drugs is crucial for a better disease management.

NF-κB and Autoimmune, Proliferative, and Inflammatory Diseases

The p65 subunit of NF-κB (also known as RelA, NFκB3 and NF-κB p65 subunit) is a member of the Rel/NF-κB family of transcription factors which includes p50, cRel, p52 and RelB. NF-κB p65 subunit was first isolated from Jurkat T cells using a probe that spanned a conserved domain to the proto-oncogene cRel (Ruben et al., *Science,* 1991, 251, 1490–1493) and since, a naturally occurring transforming variant of the protein has been shown to exist (Narayanan et al., *Science,* 1992, 256, 367–370). In addition, the NF-κB binding DNA sequence has been found in various genes and it has been shown that it is actually important for the expression of the function of genes. The binding sequence of NF-κB (κB motifs) is composed of about 10 bases having a common sequence which starts with a cluster of G (guanine) and ends with a cluster of C (cytosine) (consensus sequence 5'-GGGRNNYCCC-3'). However, a number of sequences to which DNA binding proteins can be bonded are present on the genes of interleukin-1 (to be referred to as IL-1 hereinafter in some cases) and tumor necrosis factor (to be referred to as TNF hereinafter in some cases) which are known as inflammatory proteins, and it is known that the NF-κB binding sequence is also present therein (Clark, B. D. et al., *Nucl. Acids Res.,* 14, 7898, 1984; Nedospasov, S. A. et al., *Cold Spring Harb. Symp. Quant. Biol.,* 51, 611, 1986). It has been reported that the binding of NF-κB inhibits transcription to mRNA (Hiscott, J. et al., *Mol. Cell. Biol.,* 13, 6231, 1993; Collart, M. A. et al., *Mol. Cell. Biol.,* 10,1498, 1990).

Other genes regulated by NF-κB p65 subunit-containing dimers include cytokines such as Interleukin-2, Interleukin-6, Interleukin-8, and granulocyte macrophage-colony stimulating factor (GM-CSF), adhesion molecules such as vascular cells adhesion molecule-1 (VCAM-1), endothelial leukocyte adhesion molecule-1 (ELAM-1) and intercellular adhesion molecule-1 (ICAM-1) and several acute phase response proteins (Ghosh et al., *Annu. Rev. Immunol.,* 1998, 16, 225–260). It has recently been demonstrated that the ability of NF-κB p65 subunit to activate transcription is regulated by Protein kinase A, which modulates the interaction of NF-κB p65 subunit with CBP/p300 (Zhong et al., *Mol. Cell,* 1998, 1, 661–671). More recently, molecules like chemokines such as Gro a, α, β, γ, RANTES, MCP-1/JE and enzymes such as COX-2 and iNOS were found to be regulated by NF-78 B. Compositions of non-ionic block copolymer of the present invention are effective for the treatment and prevention of diseases such as rheumatoid arthritis, systemic lupus erythematosus, systemic scleroderma, Behcet disease, periarteritis, ulcerative colitis, Crohn disease, active chronic hepatitis, glomerular nephritis and the like various autoimmune diseases; and osteoarthritis, gout, atherosclerosis, psoriasis, atopic dermatitis, pulmonary diseases with granuloma, various intractable diseases in which inflammatory symptoms such as of various types of encephalitis are the basis of the morbid state, endotoxin shock, sepsis, inflammatory colitis, diabetes, acute myelocytic leukemia, pneumonia, heart transplantation, encephalomylitis, anorexia, acute hepatitis, chronic hepatitis, drug induced hepatic injury, alcoholic hepatitis, viral hepatitis, jaundice, hepatic cirrhosis, hepatic insufficiency, atrial myxoma, Castleman syndrome, multiple myeloma, Rennert T lymphomatosis, mesangial nephritis, renal cell carcinoma, cytomegaloviral hepatitis, cytomegaloviral retinopathy, adenoviral cold syndrome, adenoviral pharyngoconjunctival fever, adenoviral ophthalmia, AIDS and the like.

Compositions of non-ionic block copolymers of the present invention may inhibit expression of genes of certain substances such as cytokines, inflammatory cytokine receptor antagonists, MHC class I, MHC class II, β2 microglobulin, immunoglobulin light chain, serum amyloid A, angiotensinogen, complement B, complement C4, C-myc gene, HIV, SV40, CMV, adenovirus and the like, so that the inventive composition is useful in treating and/or preventing various diseases in which these substances are taking roles.

It has been documented that transcription factors are involved in rheumatoid arthritis and possibly other autoimmune, proliferative, and inflammatory diseases (Manning et al., *Rheumatoid Arthritis* 1997, Vol. 1, No. 2). Altered gene expression is fundamental to the etiology of RA. Inflamed rheumatoid joints contain many activated cells including T and B lymphocytes, monocytes/macrophages, fibroblasts and endothelial cells. These cells activated display elevated expression of many genes encoding inflammatory molecules, including cytokines, cell adhesion molecules and matrix degrading enzymes. Overexpression of IL-1α, IL-1β, IL-6, IL-8, IL-10, GM-CSF, G-CSF, M-CSF, TNFα, EGF, PDGF and TGFβ has been observed in synovial cells or fluid from RA patient. T-cells seem also to play a role in RA. TNFα and IL-1, in particular, appear to play a key role in RA disease progression. The distribution of activated NF-κB in the rheumatoid joints is consistent with the pattern of expression of NF-κB genes, including endothelial cell adhesion molecules and macrophages-derived TNFα and IL-1. A method, composition, drugs that can inhibit NF-κB or any other transcription factors involved in autoimmune, proliferative, and inflammatory diseases would be of interest for clinicians.

Non-Ionic Block Copolymers

It has been discovered that the effectiveness of non-ionic block copolymers in enhancing the potency of chemotherapeutic drugs and reversing MDR is highly dependent on (a) the hydrophobe percentage and (b) on the hydrophobe molecular mass. The effectiveness increases with either an increase in the percentage (a) or an increase in weight (b), or both. These hydrophobe percentage and hydrophobe weight increases also correlate with improved micelle formation properties wherein micelle formation for these copolymers occurs at lower concentrations. See, Hunter et al., *Macromolecules* 26: 5030, 1993; Hunter et al., *Macromolecules* 26: 5592, 1993; and Alexandris et al., *Macromolecules* 27: 2414, 1994. While not wishing to be limited to a particular theory, it is believed that micelle formation serves as a surrogate for measuring the physical properties that lead to improved biological agent delivery properties.

The pharmaceutical compositions of the invention can be administered by a number of routes, including without limitation orally, topically, rectally, vaginally, by pulmonary route, for instance, by use of an aerosol, or parenterally, including but not limited to intramuscularly, subcutaneously, intraperitoneally or intravenously. The compositions can be administered alone, or can be combined with a pharmaceutically-acceptable carrier or excipient according to standard pharmaceutical practice. For the oral mode of administration, the compositions can be used in the form of tablets, capsules, lozenges, troches, powders, syrups, elixirs, aqueous solutions and suspensions, and the like. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the compositions can be combined with emulsifying and suspending agents. If desired, certain sweetening and/or flavoring agents can be added. For parenteral administration, sterile solutions of the conjugate are usually prepared, and the pHs of the solutions are suitably adjusted and buffered. For intravenous use, the total concentration of solutes should be controlled to render the preparation isotonic. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. For pulmonary administration, diluents and/or carriers will be selected to be appropriate to allow the formation of an aerosol.

Certain non-ionic block copolymers have been found to have beneficial multiple biological effects when administered to a human or animal.

1) Non-ionic block copolymers can be used as rheologic agents to treat circulatory diseases either alone or in combination with other compounds, including but not limited to, fibrinolytic enzymes, anticoagulants, free radical scavengers, anti-inflammatory agents, antibiotics, membrane stabilizers and/or perfusion media. These activities have been described in U.S. Pat. Nos. 4,801,452, 4,873,083, 4,879,109, 4,837,014, 4,897,263, 5,064,643; 5,028,599; 5,047,236; 5,089,260; 5,017,370; 5,078,995; 5,032,394; 5,041,288; 5,071,649; 5,039,520; 5,030,448; 4,997,644; 4,937,070; 5,080,894; and 4,937,070, all of which are incorporated herein by reference. The non-ionic block copolymers are thought to have a rheologic effect because they are surface-active. This property makes them useful to treat diseases and conditions in which resistance to blood flow is pathologically increased by injury due to the presence of adhesive hydrophobic proteins or damaged membranes. This adhesion is produced by pathological hydrophobic interactions and does not require of specific ligands. Such proteins and/or damaged membranes increase resistance in the microvasculature by increasing friction and reducing the effective radius of the blood vessel. It is believed that the most important of these proteins is soluble fibrin. It is believed that fibrin, especially soluble fibrin, increases adhesion of cells to one another, markedly increases friction in small blood vessels and increases viscosity of the blood, especially at low shear rates. The effects of the surface-active copolymer are believed to be essentially lubrication effects because they reduce the friction caused by the adhesion. The surface-active copolymer can be administered with a fibrinolytic enzyme, a free radical scavenger, or it can be administered alone for treatment of certain circulatory conditions that either are caused by or cause pathological hydrophobic interactions of blood components. These conditions include, myocardial infarction, stroke, bowel or other tissue infarctions, malignancies, adult respiratory distress syndrome (ARDS), disseminated intravascular coagulation (DIC), diabetes, unstable angina pectoris, hemolytic uremic syndrome, red cell fragmentation syndrome, heat stroke, retained fetus, eclampsia, malignant hypertension, burns, crush injuries, fractures, trauma producing shock, major surgery, sepsis, bacterial, parasitic, viral and rickettsial infections which promote activation of the coagulation system, central nervous system trauma, and during and immediately after any major surgery. It is believed that treatment of the pathological hydrophobic interactions in the blood that occurs in these conditions significantly reduces microvascular and other complications that are commonly observed.

2) Non-ionic block copolymers can be used as an adjuvant in a vaccine which is comprised of an antigen and an improved adjuvant. The combination of lipid conjugated polysaccharide with copolymer and an immunomodulating agent such as monophosphoryl lipid A, induces the production of a strong IgG response in which all of the subclasses of IgG are present. In particular, the IgG2 and IgG3subclasses which are protective against pneumococcal infections are predominant. This is an unexpected finding because there is no protein or peptide in the immnunogen preparation. It is believed that peptide moieties are essential for stimulating T cells which are required for production of these isotypes. Others have reported that polysaccharides are incapable of stimulating T cells. Nevertheless, the combination of copolymer, lipid conjugated polysaccharide and immunomodulating agent is able to produce such a response.

3) Non-ionic block copolymers can be used as anti-infective agents. Another group of non-ionic block copolymers inhibit the growth of bacteria and viruses. For example, these surface-active copolymers have been shown to inhibit HIV viruses, Mycobacteria species and Toxoplasma gondii. The surface-active copolymers are effective in treating a viral infection in a human or animal including infections caused by the HIV virus or related strains. The invention provides a composition that can be administered to patients who are infected with HIV viruses or similar viruses. The surface-active copolymer is effective in inhibiting or suppressing the replication of the HIV virus and related virus strains in cells. The surface-active copolymers are useful for treating infections caused by microorganisms when used alone or with a conventional antibiotic. Several conventional antibiotics that can be used with the surface-active copolymer include, rifampin, isoniazid, ethambutol, gentamicin, tetracycline, and erythromycin.

4) Non-ionic block copolymers can be used as growth stimulators and immune stimulators. Certain of the non-ionic block copolymers are capable of effecting biological systems in several different ways. The biologically-active copolymers are capable of stimulating the growth of an organism, stimulating the motor activity of an organism, stimulating the production of T-cells in the thymus, peripheral lymphoid tissue, and bone marrow cells of an animal, and stimulating immune responsiveness of poultry. The biologically-active copolymers also have a wide variety of effects on individual cells. These compounds have ionophoric activity, i.e., they cause certain ions to be transported across cell membranes. The compounds can cause non-cytolytic mast cell degranulation with subsequent histamine release. In addition, it has been found that certain members of this class of biologically-active copolymers are capable of specifically killing certain cancer cell lines. Certain of the biologically-active copolymers can be administered orally to animals to stimulate the growth of food animals such as chickens and swine.

Unexpectedly, unlike previously disclosed possible applications, the present invention discloses that compositions of certain but not all amphiphilic block copolymers are capable of inhibiting rheumatoid arthritis (see U.S. Pat. No. 5,166,219). Mechanistically, this unexpected observation could lie on the following speculations. Autoimmune diseases such as RA are dependent on cell-cell interaction, sometimes triggered by infectious diseases and heavily dependent of an immune response. The cells of the immune system turn a large number of genes on or off in regulating the selective attack of invading organisms, such as viruses and bacteria. At the same time, the immune system avoids attacking normal tissues to which it has developed a "self-tolerance." In abnormally functioning immune systems, however, the self-tolerance process can go awry resulting in the body attacking its own tissues or organs. This can result in autoimmune diseases such as rheumatoid arthritis, multiple sclerosis and diabetes. The immune system can also mount an unwelcome attack against transplanted organs, resulting in rejection of the donor organ. Currently available treatments for these conditions center around the use of drugs to suppress such unwanted immune responses. These treatments, however, are unable to provide long-lasting restoration of natural self-tolerance and also have unwanted side effects. Drug researchers have long sought ways by which to better mimic the normal process of self-tolerance to aid in the development of drugs with long-lasting and safe therapeutic effects. Thus, a non toxic, long lasting treatment like the compositions and methods described in the embodiments of the present invention are of considerable use.

SUMMARY OF THE INVENTION

The present invention provides for compositions and methods for preventing, inhibiting and treating rheumatoid arthritis and other autoimmune, proliferative and inflammatory diseases enumerated above. These include but are not limited to Hashimoto's thyroiditis, Graves' disease, Addison's disease, juvenile diabetes (Type I), myasthenia gravis, pemphigus vulgaris, sympathetic ophthalmia, multiple sclerosis, autoimmune hemolytic anemia, active chronic hepatitis, rheumatoid arthritis, thrombosis, thyroiditis, systemic lupus erythematosus, and graft rejection in humans or other animals. The present invention also provides methods of reducing inflammation, autoimmune responses or graft rejection comprising administering compositions of the present invention by intravenous, intramuscular, transdermal, oral or other introduction into the human or other animal to be treated. The present invention also provides compositions comprising at least one non-ionic block copolymer and a carrier.

DETAILED DESCRIPTION OF THE INVENTION

Nonionic Polyether Block Copolymers and Nonionic Polyether Segments.

Nonionic polyether block copolymers and polyether segments are exemplified

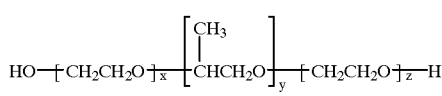

I by the block copolymers having the formulas:

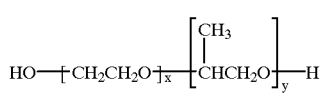

II

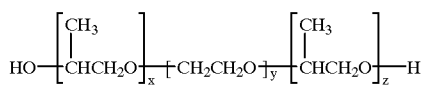

III

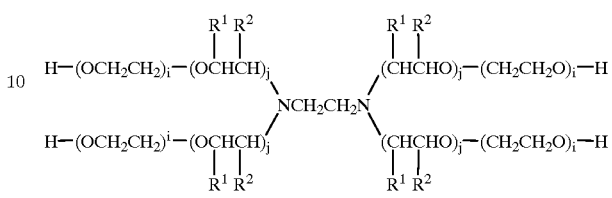

IV

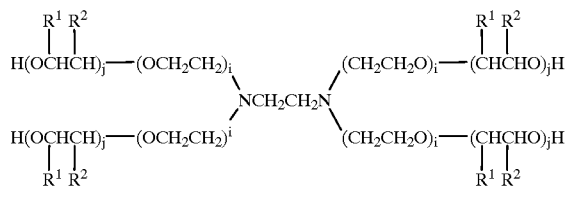

V in which x, y, z, i, and j have values from about 2 to about 800, preferably from about 5 to about 200, more preferably from about 5 to about 80, and wherein for each $R^1$, $R^2$ pair, one is hydrogen and the other is a methyl group. Formulas (I) through (III) are oversimplified in that, in practice, the orientation of the isopropylene radicals within the B block will be random. This random orientation is indicated in formulas (IV) and (V), which are more complete. Such poly(oxyethylene)-poly(oxypropylene) block copolymers have been described by Santon, Am. Perfumer Cosmet., 72(4):54–58 (1958); Schmolka, Loc. cit. 82(7): 25–30 (1967); Non-ionic Surfactants, Schick, Ed. (Dekker, N.Y., 1967), pp. 300–371. A number of such compounds are commercially available under such generic trade names as "lipoloxamers", "poloxamers", "Pluronic®", and "synperonics." poly(oxyethylene)-poly(oxypropylene) polymers within the B-A-B formula are often referred to as "reversed" Pluronic®, "Pluronic-R®" or "meroxapol."

The "polyoxamine" polymer of formula (IV) is available from BASF (Wyandotte, Mich.) under the tradename Tetronic®. The order of the polyoxyethylene and polyoxypropylene blocks represented in formula (IV) can be reversed, creating Tetronic-R®, of formula (V) also available from BASF. See, Schmolka, J. Am. Oil. Soc., 59:110 (1979). Polyoxypropylene-polyoxyethylene block copolymers can also be designed with hydrophilic blocks comprising a random mix of ethylene oxide and propylene oxide repeating units. To maintain the hydrophilic character of the block, ethylene oxide will predominate. Similarly, the hydrophobic block can be a mixture of ethylene oxide and propylene oxide repeating units. Such block copolymers are available from BASF under the tradename Pluradot™.

A number of pluronics are designed to meet the following formula:

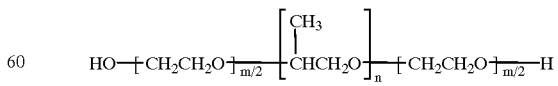

IA

The values of m and n usually will represent a statistical average and the number of repeating units of the first block of a given molecule will generally not be exactly the number of repeating units of the third block. The characteristics of a number of block copolymers,of formula (IA), are as follows:

| Copolymer | MW | Average # of oxypropylene units, n | Average # of oxyethylene units, n | HLB | CMC, $\mu M^c$ |
|---|---|---|---|---|---|
| L31 | 1100 | 17.1 | 2.5 | 5 | 1180 |
| L35 | 1900 | 16.4 | 21.6 | 19 | 5260 |
| L43 | 1850 | 22.3 | 12.6 | 12 | 2160 |
| L44 | 2200 | 22.8 | 20.0 | 16 | 3590 |
| L61 | 2000 | 31.0 | 4.5 | 3 | 110 |
| L62 | 2500 | 34.5 | 11.4 | 7 | 400 |
| L64 | 2900 | 30.0 | 26.4 | 15 | 480 |
| F68 | 8400 | 29.0 | 152.7 | 29 | 480 |
| L81 | 2750 | 42.7 | 6.2 | 2 | 23 |
| P84 | 4200 | 43.4 | 38.2 | 14 | 71 |
| P85 | 4600 | 39.7 | 52.3 | 16 | 65 |
| F87 | 7700 | 39.8 | 122.5 | 24 | 91 |
| F88 | 11400 | 39.3 | 207.8 | 28 | 250 |
| L92 | 3650 | 50.3 | 16.6 | 6 | 88 |
| F98 | 13000 | 44.8 | 236.4 | 28 | 77 |
| L101 | 3800 | 58.9 | 8.6 | 1 | 2.1 |
| P103 | 4950 | 59.7 | 33.8 | 9 | 6.1 |
| P104 | 5900 | 61.0 | 53.6 | 13 | 3.4 |
| P105 | 6500 | 56.0 | 73.9 | 15 | 6.2 |
| F108 | 14600 | 50.3 | 265.4 | 27 | 22 |
| L121 | 4400 | 68.2 | 10.0 | 1 | 1 |
| P123 | 5750 | 69.4 | 39.2 | 8 | 4.4 |
| F127 | 12600 | 65.2 | 200.4 | 22 | 2.8 |

The average numbers of oxyethylene and oxypropylene units in the foregoing were calculated using the average molecular weighs (MW) provided by the manufacturer. The hydrophilic-lipophilic balance (HLB) of the copolymers were determined by the manufacturer (BASF Co.). The critical micelle concentrations (CMC) were determined at 37° C. by the surface tension method described in al., *Macromolecules* 28: 2303–2314 (1995).

Some other specific poly(oxyethylene)-poly(oxypropylene) block copolymers relevant to the invention include:

| No. | Block Copolymer | Hydrophobe Weight | Hydrophobe Percentage |
|---|---|---|---|
| 1 | F38 | 900 | 20% |
| 2 | L42 | 1200 | 80% |
| 3 | L63 | 1750 | 70% |
| 4 | P65 | 1750 | 50% |
| 5 | L72 | 2050 | 80% |
| 6 | F75 | 2050 | 50% |
| 7 | P77 | 2050 | 30% |
| 8 | L122 | 4000 | 80% |
| 9 | 10R5 | 1000 | 50% |
| 10 | 10R8 | 1000 | 20% |
| 11 | 12R3 | 1200 | 70% |
| 12 | 17R1 | 1700 | 90% |
| 13 | 17R2 | 1700 | 80% |
| 14 | 17R4 | 1700 | 60% |
| 15 | 17R8 | 1700 | 20% |
| 16 | 22R4 | 2200 | 60% |
| 17 | 25R1 | 2500 | 90% |
| 18 | 25R2 | 2500 | 80% |
| 19 | 25R4 | 2500 | 60% |
| 20 | 25R5 | 2500 | 50% |
| 21 | 25R8 | 2500 | 50% |
| 22 | 31R1 | 3100 | 90% |
| 23 | 31R2 | 3100 | 80% |
| 24 | 31R4 | 3100 | 60% |
| 25 | 304 | 500 | 60% |
| 26 | 504 | 1100 | 60% |
| 27 | 701 | 2200 | 90% |
| 28 | 702 | 2200 | 80% |
| 29 | 704 | 2200 | 60% |
| 30 | 707 | 2200 | 30% |
| 31 | 901 | 3300 | 90% |
| 32 | 904 | 3300 | 60% |
| 33 | 908 | 3300 | 20% |
| 34 | 1101 | 4400 | 90% |
| 35 | 1102 | 4400 | 80% |
| 36 | 1104 | 4400 | 60% |
| 37 | 1107 | 4400 | 30% |
| 38 | 1301 | 5500 | 90% |
| 39 | 1302 | 5500 | 80% |
| 40 | 1304 | 5500 | 60% |
| 41 | 1307 | 5500 | 30% |
| 42 | 1501 | 7000 | 90% |
| 43 | 1502 | 7000 | 80% |
| 44 | 1504 | 7000 | 60% |
| 45 | 1508 | 7000 | 20% |
| 46 | 50R1 | 2100 | 90% |
| 47 | 50R4 | 2100 | 60% |
| 48 | 50R8 | 2100 | 20% |
| 49 | 70R1 | 3000 | 90% |
| 50 | 70R2 | 3000 | 80% |
| 51 | 70R4 | 3000 | 60% |
| 52 | 90R1 | 3900 | 90% |
| 53 | 90R4 | 3900 | 60% |
| 54 | 90R8 | 3900 | 20% |
| 55 | 110R1 | 4800 | 90% |
| 56 | 110R2 | 4800 | 80% |
| 57 | 110R7 | 4800 | 30% |
| 58 | 130R1 | 5700 | 90% |
| 59 | 130R2 | 5700 | 80% |
| 60 | 150R1 | 6700 | 90% |
| 61 | 150R4 | 6700 | 60% |
| 62 | 150R8 | 6700 | 20% |

The diamine-linked block copolymer of formula (IV) can also be a member of the family of diamine-linked polyoxyethylene-polyoxypropylene polymers of formula:

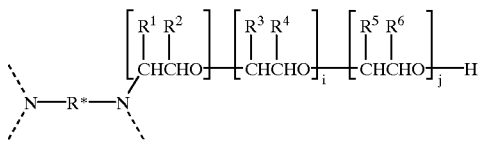

wherein the dashed lines represent symmetrical copies of the polyether extending off the second nitrogen, R* an alkylene of about 2 to about 6 carbons, a cycloalkylene of about 5 to about 8 carbons or phenylene, for $R^1$ and $R^2$, either (a) both are hydrogen or (b) one is hydrogen and the other is methyl, for $R^3$ and $R^4$ either (a) both are hydrogen or (b) one is hydrogen and the other is methyl, if both of $R^3$ and $R^4$ are hydrogen, then one $R^5$ and $R^6$ is hydrogen and the other is methyl, and if one of $R^3$ and $R^4$ is methyl, then both of $R^5$ and $R^6$ are hydrogen.

The hydrophobic/hydrophilic properties of a given block copolymer depends upon the ratio of the number of oxypropylene groups to the number of oxyethylene groups. For a composition containing a single block copolymer of poly(oxyethylene)-poly(oxypropylene), for example, this relationship, taking into account the molecular masses of the central hydrophobic block and the terminal hydrophilic blocks, can be expressed as follows:

$$n = \frac{H}{L} \cdot 1.32$$

in which H is the number of oxypropylene units and L is the number of oxyethylene units. In the general case of a block copolymer containing hydrophobic B-type segments and hydrophilic A-type segments, the hydrophobic-hydrophilic properties and micelle-forming properties are related to the value n as defined as:

$$n = (|B|/|A|) \times (b/a)$$

where $|B|$ and $|A|$ are the number of repeating units in the hydrophobic and hydrophilic blocks of the copolymer, respectively, and b and a are the molecular weights for the respective repeating units.

Selecting a block copolymer with the appropriate n value will depend upon the hydrophobic/hydrophilic properties of the specific agent, or the composite hydrophilic/hydrophobic properties of a mixture of agents to be formulated. Typically, n will range in value from about 0.2 to about 9.0, more preferably between about 0.25 and about 1.5. This range should be viewed not as numerically critical but as expressing the optimum hydrophobic/hydrophilic balance between the predominantly hydrophilic poly(oxyethylene) blocks, and the predominantly hydrophobic poly(oxypropylene) blocks.

An important aspect of the present invention-involves utilizing mixture of different block-copolymers of poly(oxyethylene)-poly(oxypropylene) to achieve a more specific hydrophobic-hydrophilic balance suitable for a given cytokine or mixture of several cytokines, preserving the optimal size of particles. For example, a first block copolymer may have an n of 1.0 whereas a second may have a value of 1.5. If material having an n of 1.3 is desired, a mixture of one weight portion of the first block copolymer and 1.5 weight portion of the second block-copolymer can be employed.

Thus, a more generalized relationship for such mixtures can be expressed as follows:

$$N = 1.32 \cdot \left[ \frac{H_1 \cdot m_1}{(L_1) \cdot (m_1 + m_2)} + \frac{H_2 \cdot m_2}{(L_2) \cdot (m_1 + m_2)} \right]$$

in which $H_1$ and $H_2$ are the number of oxypropylene units in the first and second block copolymers, respectively; $L_1$ is the number of oxyethylene units in the first block copolymer; $L_2$ is the number of oxyethylene units in the second block copolymer; $m_1$ is the weight proportion in the first block-copolymer; and $m_2$ is the weight proportion in the second block copolymer.

An even more general case of a mixture of K block copolymers containing hydrophobic B-type block copolymers and hydrophilic A-type block copolymers, the N value can be expressed as follows:

$$N = \frac{b}{a} \sum_{i=1}^{k} \left( \frac{|B|_i}{|A|_i} \cdot \frac{m_i}{M} \right)$$

where $|A|_i$ and $|B|_i$ are the numbers of repeating units in the hydrophilic (A-type) and hydrophobic (B-type) blocks of the i-th block copolymer, m is the weight proportion of this block copolymers, M is the sum of weight proportions of all block copolymers in the mixture, $$\left( M = \sum_{i=1}^{k} m_i \right).$$

and a and b are the molecular weights for the repeating units of the hydrophilic and hydrophobic blocks of these block copolymers respectively.

If only one block copolymer of poly(oxyethylene)-poly(oxypropylene) is utilized, N will equal n. An analogous relationship will apply to compositions employing more than two block copolymers of poly(oxyethylene)-poly(oxypropylene).

Where mixtures of block copolymers are used, a value N will be used, which value will be the weighted average of n for each contributing copolymers, with the averaging based on the weight portions of the component copolymers. The value N can be used to estimate the micelle-forming properties of a mixture of copolymers. The use of the mixtures of block copolymers enhances solubility and prevents aggregation of more hydrophobic block copolymers in the presence of the serum proteins. Particularly, poly(oxyethylene)-poly(oxypropylene) block copolymers with the ethylene oxide content of more than 50% solubilize hydrophobic block copolymers with ethylene oxide content of no more than 50%. In such mixtures, the preferred ratio of the hydrophilic and hydrophobic copolymer is at least 2:1 (w/w), preferably at least 5:1 (w/w), still more preferably at least 8:1 (w/w)." When copolymers other than polyethylene oxide-polypropylene oxide copolymers are used, similar approaches can be developed to relate the hydrophobic/hydrophilic properties of one member of the class of polymers to the properties of another member of the class.

Using the above parameters, one or more block copolymers of poly(oxyethylene)-poly(oxypropylene) are combined so as to have a value for N of from about 0.1 to about 9, more preferably from about 0.25 to about 1.5. The combined copolymers form micelles, the value of N affecting in part the size of the micelles thus produced. Typically, the micelles will have an average diameter of from about 10 to about 25 nm, although this range can vary widely. The average diameter of any given preparation can be readily determined by quasi-elastic light scattering techniques.

In a preferred embodiment, the block copolymer conforms to one of the following formulae:

$$A-B-A' \quad (IX)$$

$$A-B, \quad (X)$$

$$B-A-B', \text{ or} \quad (XI)$$

$$L(R^1)(R^2)(R^3)(R^4) \quad (XII)$$

wherein A and A' are A-type linear polymeric segments, B and B' are B-type linear polymeric segments, and $R^1$, $R^2$, $R^3$, and $R^4$ are either block copolymers of formulas (IX), (X), or (XI), or hydrogen and L is a linking group, with the proviso that no more than two of $R^1$, $R^2$, $R^3$, or $R^4$ are hydrogen.

The block copolymers utilized in the invention will typically, under certain circumstances, form micelles of from about 10 nm to about 100 nm in diameter. Micelles are supramolecular complexes of certain amphiphilic molecules that form in aqueous solutions due to microphase separation of the nonpolar portions of the amphiphiles. Micelles form when the concentration of the amphiphile reaches, for a given temperature, a critical micellar concentration ("CMC") that is characteristic of the amphiphile. Such micelles will generally include from about 10 to about 300 block copolymers. By varying the sizes of the hydrophilic and hydrophobic portions of the block copolymers, the tendency of the copolymers to form micelles at physiological conditions can be varied. The micelles have a dense core formed by the water insoluble repeating units of the B blocks and charge-neutralized nucleic acids, and a hydrophilic shell formed by the A blocks. The micelles have translational and rotational freedom in solution, and solutions containing the micelles have low viscosity similar to water. Micelle formation typically occurs at copolymer concentrations from about 0.001 to 5% (w/v). Preferred compositions comprise copolymers with CMC less than 0.5% wt., more preferred less than 0.1% wt. still more preferred less than 0.05% wt. Conversely materials having a higher CMC, as for example F68, are not preferred. CMC values can be determined at 25° C. using pyrene as fluorescent probe as described in Kabanov et al., *Macromolecules* 28: 2303–2314 (1995).

At high concentrations (and appropriate temperatures), some of the block copolymers utilized in the invention will form gels. These gels are viscous systems in which the translational and rotational freedom of the copolymer molecules is significantly constrained by a continuous network of interactions among copolymer molecules. Block copolymers utilized in this invention such as poly(oxyethylene)-poly (oxypropylene) copolymers have very rich phase diagrams. For example, there is extensive literature available on the phase behavior of Pluronic-water binary mixtures and Pluronic-water-oil tertiary mixtures (Wanka, G. et al., *Macromolecules*, 27, 4145, 1994, Alexandridis, P., et al., *Amphiphilic Block Copolymers. Self-Assembly and Applications*, Alexandridis, P. and Lindman, B., Eds, Elsevier, Amsterdam, Lausanne, New York, Oxford, Shannon, Singapore, Tokyo, 1999, 169). Along with isotropic solutions, these mixtures form a variety of lyotropic mesophases, including cubic, hexagonal and lamellar phases commonly called "gels" Furthermore, they reveal a thermotropic behavior, i.e. with variation in temperature, reversible transitions between various mesophases or between mesophases and isotropic solution occur. Aqueous solutions of block copolymers are characterized by a lower critical solution temperature behavior (LCST) and demonstrate phase separation at elevated temperatures. The decrease in the solubility of block copolymers with increased temperature is explained by the dehydration of poly(oxyethylene) and poly(oxypropylene) blocks. In gels, microsegregation of the B block repeating units may or may not occur. To avoid the formation of gels, polymer concentrations (for both block copolymers and polyether/polycation polymers) will preferably be below about 15% (w/v), more preferably below about 10%, still more preferably below about 5%. Gel formation in the block copolymer compositions such as compositions comprising poly(oxyethylene)-poly (oxypropylene) copolymers reveals thermotropic behavior and is commonly induced by increase of the temperature, for example from room temperature to the body temperature. The temperature and concentration controlled transitions are strongly dependent on the structure of the block copolymer, particularly on the ratio of the hydrophobic and hydrophilic segments (Wanka, G. et al, *Macromolecules*. 27, 4145, 1994; Alexandndis, P., et al., *in Amphiphilic Block Copolymers. Self-Assembly and Applications*. Alexandridis, P. and Lindmen, 8., Eds, Elsevier, Amsterdam, Lousanne, New York, Oxford, Shannon, Singapore, Tokyo, 1999, 169). It is preferred that the gels be avoided. Therefore compositions that do not form gels, and methods of treatment comprising administration of such compositions are preferred.

F127/L61 at 2.25% W:V (8:1 W:W) acts as an immunomodulator in pathological conditions like rheumatoid arthritis and in inflammation while it does not exhibit the immunomodulator effect under normal physiological conditions (see Example 1). In addition, to obtain and observe the immunodulator effect, F127/L61 at 2.25% W:V (8:1 W:W) has to be used at a high dose (>450mg/kg). The first example to support the statement that F127/L61 at 2.25% W:V (8:1 W:W) is a potential immunomodulator for the treatment of rheumatoid arthritic patient is shown in the experiment when F127/L61 at 2.25% W:V (8:1 W:W) was used to reduce basal levels of circulating systemic TNFα in normal and healthy animals (Example 6). We found that following administration of F127/L61 at 2.25% W:V (8:1 W:W) in normal animals that there was a slight reduction of basal level of circulating TNFα. This reduction can be considered modest since in fully immuno-competent animals the TNFα levels are extremely low and almost below the detection limit of commercial ELISA kits. F127/L61 at 2.25% W:V (8:1 W:W) reduced the basal levels of TNFα in normal animals but not to the extent to that observed in animals under a pathological condition. In contrast to normal and healthy animals, we found that F127/L61 at 2.25% W:V (8:1 W:W) had a more striking inhibitory effect in animals to which lipopolysaccharide (LPS) was injected to trigger a septic shock that leads to a massive production and release of TNFα along with many other cytokines (Examples 7 to 9) somehow mimicking an acute arthritic condition. In this situation, F127/L61 at 2.25% W:V (8:1 W:W) was shown to reduce the LPS-induction of TNFα, which suggests an inhibitory effect. As opposed to the basal level experiment, this experiment suggests that F127/L61 at 2.25% W:V (8:1 W:W) has a more striking effect in sick animals rather than normal animals. Finally, the fact that F127/L61 at 2.25% W:V (8:1 W:W) was more efficacious in the CIA model in mouse (less agressive) than in the adjuvant model in rats (more agressive) suggests that the treatment may be beneficial for patients with an early onset of the disease.

The only population of cells that may be potentially affected by F127/L61 at 25 2.25% W:V (8:1 W:W) are macrophages. Some laboratories have shown that non-ionic block copolymers have some immunomodulator effect that could be used in some conditions like tumor. Moghimi et al. have injected poloxamers in LPS-nonresponders C3H/HeJ mice known to be resistant to all known in vivo and in vitro effect of LPS which in a way mimicks an immunodeficient condition in mice. In these mice, poloxamers had the effect of increasing phagocytic activity of macrophages in tissues like liver, spleen, and lymph nodes. Their conclusion was that this activation could lead to stimulation of macrophage function to destroy tumor cells. The monocyte/macrophage defense system exerts a regulatory influence over the course and pattern of tumor development and growth. Moghimi et al., *J. Nat'l Cancer Inst.* 1996; 88(11):766–8. Macrophages stimulation before or during the early stages of tumor growth can attenuate tumor growth and spread, whereas suppression of macrophage function can accelerate tumor growth (1). The stimulation effect could be beneficial to rheumatoid arthritis since this disease, like cancer, is dependent on cellular proliferation, angiogenesis and inflammation. In addition, it has been reported the induction of Ia (MHC II) in macrophages. Howerton et al., *J. Immunol* 1990; 144(5):1578–84. More specifically, the authors found that non-ionic block copolymers caused the following; 1) macrophages to increase their phagocytic ability, 2) a 7-fold increase in the levels of Ia on macrophages in both normal and athymic nude mice—so it is not necessarily a T cell dependent process, 3) an overall increase in the number of macrophages, suggesting an active process, 4) a synthesis of Ia by the macrophages, 5) increase secretion of superoxide by these macrophages, i.e. priming for microbicidal activity, 6) macrophages did not spontaneously lyse tumor cells, so are not fully active, but they could be induced to do so by IFNγ, LPS or any other proinflammatory cytokines which can be found in vivo especially in conditions like acute inflammation or more specifically like in rheumatoid arthritis in which IL-1and TNF are now known to be the major proinflammatory cytokines accompanying the progression of the disease. Previously the same authors found that not all poloxamers that differ in the size of their constituent blocks of polyoxyethylene and polyoxypropylene can activate and induce Ia. This observation suggests that F127/L61 at 2.25% W:V (8:1 W:W) is likely to be active in patients with an arthritic condition since activated macrophages with an increase capacity to phagocytose may result in the removal of immune complexes from the blood or the disease site (inflamed joints containing activated T-cells and neutrophils) and an antiinflammatory response. Thus neutrophil activation was recently reported to be inhibited by a component of F127/L61 at 2.25% W:V (8:1 W:W) called F127. Jackson et al. *Biomaterials* 2000; 21(14):1483–91

The anti-inflammatory properties of non-ionic block copolymers were tested in an immunologically-mediated disease model. They were tested using in vivo models mimicking certain human inflammatory diseases, such as autoimmune arthritis. Collagen-induced arthritis (CIA) is an autoimmune arthritic disease, Stuart, J. M., et al., *Ann. Rev. Immunol.* 2:199–218, 1984, readily elicited in certain strains of rodents and sub-human primates by immunization with chick type 11 collagen emulsified in CFA. CIA exhibits many of the histological features observed in patients with rheumatoid arthritis (RA), including infiltration and proliferation of mononuclear cells, synovial hyperplasia, pannus formation, and often severe osteolysis with destruction of joint cartilage and architecture. CIA pathology is dependent on cell-mediated immunity, Levin E., U.S. Pat. No. 4,031,376, and production of lymphokines such as IFN.gamma., Mauritz, et al., *Arth Rheum.*, 31:1297–1304, 1988. The development of CIA and RA is accompanied by the production of antibodies reactive with type 11 collagen, particularly those isotypes that can activate the complement cascade, Watson, et al., *J. Exp Med.* 162:1878–1891, 1985, Watson, et al., *Arth. Rheum.* 29:1316–1321, 1986. In the murine model, high levels of IgG2a anti-collagen antibody are associated with CIA susceptibility and course of disease. Similarly, patients with RA exhibit substantial levels of complement-fixing IgG3 anti-type II collagen antibodies. Passive transfer studies have demonstrated that the Ig fraction from serum of mice with CIA (containing high levels of IgG2a), or from serum of patients with RA (containing high levels of IgG3), can initiate a transient arthritis in normal murine recipients, Stuart, et al., *Ann. Rev. Immunol.* 2:199–218, 1984. The usefulness of CIA as a model for arthritis also stems from its dependence on inflammatory mediators and processes, Griswold, et al., *Arth. Rheum.* 31:1406–1412, 1988, a potential focus for the beneficial effects of a composition of block copolymers.

EXAMPLE 1

Suppression of Rheumatoid Arthritis Development with a Combination of Non-Ionic Block Copolymers The anti-RA efficacy of SP1018R (200 μl of F127 and L61 in a ratio of 8:1 at a concentration of 2.25%) was compared to that of MTX that was given at a human equivalent dose (0.1 mg/kg i.v.), both drugs were given on day 30 and day 37 after the first immunization with collagen. For induction of severe CIA, mice were primed with 500 μl pristane and immunized at day 14 and 21 by administration of 100 μg colagen type II in Freund's complete adjuvant. The control (placebo) and the treated animals were evaluated for RA severity. RA was graded semi-quantitatively on a scale of 0–4 for each paw: 0=no changes; 0.5=significant swelling and redness on one digit; 1=swelling and erythema of 2 digits; 2=mild swelling and erythema of the limb or swelling of more than 2 digits; 3=marked swelling and erythema of the limb; and 4=maximal swelling and redness of the limb and later, ankylosis. Table I shows that although animals treated with MTX revealed a slight therapeutic effect as previously reported elsewhere, both control and MTX treated groups had progressive increase in clinical disease symptoms. The animals receiving SP1018R demonstrated no development of symptoms. As noted by others, Stuart, J. M., et al., *Ann. Rev. Immunol.* 2:199–218, 1984, Collagen-immunized DBA/I mice exhibit disease induction starting at about 20 days post-immunization, and peeking at about 50–60 days into the experiment. Histologic analysis (not shown) confirmed extensive mononuclear infiltration and pannus formation as reported by others using similar techniques, Wooley, et al., *J. Exp. Med.* 154:688–700, 1981. Arthritis was usually noted in the hind limbs, but a substantial fraction of the mammals exhibited disease in all four limbs. The cumulative incidence of arthritis was 100% of the immunized mice (Wooley, et al., loc. cite).

Despite the variation in terms of RA symptoms development, we can see that out of 3 experiments, F127/L61 at 2.25% W:V (8:1 W:W) had an inhibitory effect on RA. The data shown below represent the maximal frequency (%) of animals having developed symptoms of RA and the frequency of animals still having the symptoms of RA at the end of the study. All Pluronics used in all examples were purchased from BASF Co.

Frequency of RA development at various time points during the course of RA development

| Study No. | Saline | | F127/L61 at 2.25% W:V (8:1 W:W) (2X) | | Other | |
|---|---|---|---|---|---|---|
| | Max | End of Study | Max | End of Study | Max | End of Study |
| NG2 56 | 100% | 100% | 43% | 0% | MTX—100% | 100% |
| NG3 27 | 100% | 50% | 50% | 0% | — | — |
| NG3 48 | 43% | 43% | 13% | 0% | F127/L61 at 2.25% W:V (8:1 W:W) (1X)—50% | 50% |

EXAMPLE 2

SP1018R Selectively Suppress Immune Reactions to Collagen

C57Bl/6 mice were immunized with collagen type II as described in the previous example and then treated with SP1018R (200 µl of F127 and L61 in a ratio of 8:1 at a concentration of 2.25% ) one week after the second immunization. Mice were treated either once with SP1018R or once a week during 3 weeks. Sera were collected 4 weeks after the first SP1018R treatment and tested for the presence of specific anti-collagen antibodies using ELISA. The data shown in table II suggests that SP1018R significantly reduces humoral immune response to collagen. The effect of SP1018R on cellular immune response is being presently evaluated.

| Treatment | Mean titers of antibody anti-collagen type II |
|---|---|
| Non-treated (placebo) | 1:6000 +/− 1:2500 |
| Treated 1× with SP1018R | 1:3000 +/1 1:1000 |
| Treated 3× with SP1018R | 1:2500 +/1 1:1000 |

EXAMPLE 3

SP1018R Used To Suppress Systemic Lupus Erythematosus

Immune-mediated nephritis is a common complication of systemic lupus erythematosus (SLE). It is now clear that multiple and independent mechanisms contribute to disease onset and pathogenesis, which may explain the remarkable phenotypic and histopathological heterogeneity observed in human SLE. Identification and characterization of disease-relevant autoantibodies, cellular effectors, and soluble immune elements have provided crucial insight into the immunologic interactions that promote renal immune injury. It is now clear that nephritogenic autoantibodies of diverse specificity localize to the kidney by a variety of mechanisms. They are accompanied by activated macrophages and T cells recruited in part through enhanced and abnormal production of macrophage growth factors and cytokines. These pathways provide novel targets for therapeutic intervention to prevent or ameliorate the aggressive autoimmune nephritis that characterizes SLE.

F.sub.1 hybrids of autoimmune New Zealand black (NZB) mice and the phenotypically normal New Zealand White (NZW) mouse strain develop severe systemic autoimmune disease, more fulminant than that found in the parental NZB strain. These mice manifest several immune abnormalities, including antibodies to nuclear antigens and subsequent development of a fatal, immune complex-mediated glomerulonephritis with female predominance, remarkably similar to SLE in humans. Knight, et al., (1978) *J. Exp. Med.* 147:1653, which is incorporated hereby by reference. In both the human and murine forms of the disease, a strong association with MHC gene products has been reported. HLA-DR2 and HLA-DR3individuals are at a higher risk than the general population to develop SLE (Reinertsen, et al., (1970) *N. Engl. J. Med.* 299:515), while in NZB/W F.sub.1 mice (H-2.sup.d/u), a gene linked to the h-2.sup.u haplotype derived from the NZW parent contributes to the development of the lupus-like nephritis. The effect of non-ionic block copolymers (SP1018R) described in the invention can be measured by survival rates and by the progress of development of the symptoms, such as proteinuria and appearance of anti-DNA antibodies.

EXAMPLE 4

SP1018R Used To Suppress Experimental Autoimmune Encephalomyetitis

Immunohistochemistry studies with macrophage markers shows that in this disease different populations of macrophages (i.e. perivascular cells, microglia and infiltrating blood-borne macrophages) are present in the central nervous system. These subpopulations partially overlap in some functional activity while other activities seem to be restricted to a distinct subpopulation, indicating that these subpopulations have different roles in the pathogenesis of encephalomyelitis. Studies revealed that immunocytochemical and morphological studies, combined with new techniques such as in situ nick translation and experimental approaches like the use of bone marrow chimeras and macrophage depletion techniques, give valuable information about the types and functions of cells involved in central nervous system inflammation. Multiple sclerosis (MS) is a chronic inflammatory CNS disorder caused by demyelination in the brain and spinal cord. The disease is characterized by progressive CNS dysfunction, including muscular weakness, tremor, incontinence, ocular disturbances, and mental dysfunction, with remissions and exacerbations. Experimental allergic encephalomyelitis (EAE) induced by injection of guinea pig myelin basic protein (MBP) or MBP peptide fragments is reported to be a useful model for MS. See, for example, D. E. McFarlin et al., *J. Immun.*, 11(2): 712–715 (1974).

In this experiment, the ability of SP1018R to prevent MBP-induced EAE is tested. Female, Lewis rats of 8 weeks of age (180–250 g) are weighed and then given two intra-dermal injections (0.1 mL each) of 0.4 mg of M. tuberculin in 0.1 mL incomplete Freunds adjuvant and 50 mg of myelin basic protein in 0.1 mL of saline into the base of the tail. Animals are weighed daily and given a clinical score beginning on Day 8, post inoculation, according to the following criteria: 0.0=No illness, 0.5=Tip of tail flaccid, 1.0=Entire tail flaccid, 1.5=Hind limb weakness, 2.0=Hind limb paralysis, 2.5=Hind limb paralysis and front limb weakness, 3.0=Hind and front limb paralysis, 4.0=Moribund state or death. On day 3, post-inoculation animals are administered b.i.d either a test compound (100 mg/kg) or SP1018R by oral gavage or i.v. up to and including day 16.

EXAMPLE 5

Inhibition of transcription with F127/L61 at 2.25% W:V (8:1 W:W)

In this experiment, F127/L61 at a concentration of 2.25% W:V (8:1 W:W) is used to test its effect on gene expression (transciption) in muscle (tibialis anterior) of C57Bl/6 (6–7 week-old) female mice kept by groups of 4 and fed ad libidum. Five μg of CMV-driven plasmid DNA encoding for luciferase is formulated with block copolymers and injected i.m. into the tibialis anterior muscle. Before each intramuscular injection, the mice are anesthetized with a mixed solution of ketamine and xylazine. Mice are sacrificed 5 days following the i.m. injection and each injected muscle is dissected and rapidly homogenized with a tissue grinder (Kontes Glass Co.) in cell lysis buffer (Promega Corporation) supplemented with protease inhibitors. The extraction mixture is kept on ice for 30 minutes and then centrifuged at a maximum speed for 2 minutes. The supernatents are kept and analyzed for luciferase activity. The assay is done as follows: 20 μl of supernatent is added to luminometric tubes containing 100 μl of luciferase substrate (Promega Corporation). Light emission is measured with a luminometer (Berthold) for a period of 5 seconds. The data is reported in relative light units per second per tibialis anterior. As shown in the table below, F127/L61 at 2.25% W:V (8:1 W:W) inhibits gene expression (transcription) measured after 5 days post-injection when used at higher concentration.

| Conditions | % of luc activity |
|---|---|
| F127/L61 at 0.01% W:V (8:1 W:W) | 100 |
| F127/L61 at 0.05% W:V (8:1 W:W) | 91 |
| F127/L61 at 0.1% W:V (8:1 W:W) | 52 |
| F127/L61 at 1% W:V (8:1 W:W) | 4 |
| F127/L61 at 2.25% W:V (8:1 W:W) | 0 |

EXAMPLE 6

Inhibition of TNFα Following Systemic Treatment with

F127/L61 at 2.25% W:V (8:1 W:W).

In this experiment, F127/L61 at 2.25% W:V (8:1 W:W) is used to test its effect on basal circulating TNFα. C57Bl/6 (6–7 week-old) female mice kept by groups of 4 and fed ad libidum. Mice received i.v. 200 ul of F127/L61 at 2.25% W:V (8:1 W:W) or saline. Mice were bled at various time points following F127/L61 at 2.25% W:V (8:1 W:W) treatment. Murine TNFA levels were measured in plasma with an ELISA kits from R&D systems. The data suggest that F127/L61 at 2.25% W:V (8:1 W:W) reduces circulating TNFα below the detectable limit as compared to control mice treated with saline.

| Time point (hours) following F127/L61 at 2.25% W:V (8:1 W:W) treatment | TNFα levels in saline-treated mice (pg/mL) | TNFα levels in F127/L61 at 2.25% W:V (8:1 W:W)-treated mice (pg/mL) |
|---|---|---|
| 6 | 29.3 (±7 SEM) | Not detectable |
| 24 | 18.5 (±7 SEM) | Not detectable |
| 48 | 29.3 (±8 SEM) | Not detectable |

EXAMPLE 7
Reduction of LPS-induced TNFα with F127/L61 at 2.25% W:V (8:1 W:W)

These studies were design to test whether F127/L61 at 2.25% W:V (8:1 W:W) could reduce an induced production of systemic TNFα. The tables below summarize the data of experiments in which F127/L61 at 2.25% W:V (8:1 W:W) was administered 2 hours prior the LPS induction of TNFα. LPS was given I.P. at 5 ug i.p. and blood samples were collected after 1 hour (peak of TNFα αproduction) and 4 hours. The data tabulated in Examples 7 to 9 are showing that LPS-induced TNFα production is partially reduced with F127/L61 at 2.25% W:V (8:1 W:W) and this, when the amount of injected LPS was below the threshold causing a lethal toxic shock.

| Conditions | Time | TNFα (pg/mL) Mean | SEM |
|---|---|---|---|
| LPS alone | 1 h | 1884.5 | 95 |
|  | 4 h | 279 | 8.5 |
| LPS + F127/L61 at 2.25% w:v (8:1 w:w) | 1 h | 1145.9 | 343.6 |
|  | 4 h | 135 | 3.1 |

EXAMPLE 8

Reduction of TNF levels with F127/L61 at 2.25% W:V (8:1 W:W) following LPS Treatment (50 μg)

The tables below summarize the data of experiments in which F127/L61 at 2.25% W:V (8:1 W:W) was administered 2 hours prior the LPS induction of TNFα. LPS was given I.P. At 50 μg i.p. And i.v. and blood samples were collected after 1 hour (peak of TNFα production) and 4 hours. The data tabulated in Examples 7 to 9 are showing that LPS-induced TNFα production is partially reduced with F127/L61 at 2.25% W:V (8:1 W:W) and this, when the amount of injected LPS was below the threshold causing a lethal toxic shock.

| Conditions | Route | TNFα (pg/mL) Mean | SEM |
|---|---|---|---|
| LPS alone-4 h | I.V. | 443.4 | 48.929 |
|  | I.P. | 557 | 0.714 |
| LPS + F127/L61 at 2.25% w:v (8:1 w:w)-4 h | I.V. | 383.4 | 119.643 |
|  | I.P. | 369.5 | 20.357 |

EXAMPLE 9

Reduction of TNFα levels with F127/L61 at 2.25% W:V (8:1 W:W) following LPS treatment (200μg)

The tables below summarize the data of experiments in which F127/L61 at 2.25% W:V (8:1 W:W) was administered 2 hours prior the LPS induction of TNFα. LPS was given I.P. at 200 μg I.P. and blood samples were collected after 1 hour (peak of TNFα production) and 4 hours. The data tabulated in Examples 7 to 9 are showing that LPS-induced TNFA production is partially reduced with F127/L61 at 2.25% W:V (8:1 W:W) and this, when the amount of injected LPS was below the threshold causing a lethal toxic shock.

| Conditions | Time Hours | TNFα (pg/mL) Mean | SEM |
|---|---|---|---|
| LPS alone | 1 | 4800.6 | 816.4 |
|  | 4 | 674.6 | 121.1 |
| LPS + F127/L61 at 2.25% w:v (8:1 w:w) | 1 | 4717.1 | 1512.9 |
|  | 4 | 452.8 | 126.4 |

EXAMPLE 10

Prophylactic treatment of RA with F127/L61 at 2.25% W:V (8:1 W:W) in adjuvant arthritis model Rats were treated i.v. on day one with 1 mL of F127/L61 at 2.25% W:V (8:1 W:W) and induced for arthritis with Freund Adjuvant 10 mg of mycobactrium tuberculosis/mL and retreated i.v. with the same dose of F127/L61 at 2.25% W:V (8:1 W:W) on days seven and fourteen. The percentage of rats with disease was scored over time. The data are summarised below:

| Days | Saline (%) | F127/L61 at 2.25% W:V (8:1 W:W) (%) |
|---|---|---|
| −1 | 0 | 0 |
| 0 | 0 | 0 |
| 7 | 0 | 0 |
| 14 | 0 | 0 |
| 17 | 18.8 | 0 |
| 21 | 75 | 55 |
| 28 | 81.3 | 65 |
| 35 | 100 | 100 |

EXAMPLE 11

Therapeutic mode with F127/L61 at 2.25% W:V (8:1 W:W) on RA in adjuvant arthritis model Rats were induced for arthritis (5 per group) with Freund Adjuvant 10 mg of mycobactrium tuberculosis/mL and treated i.v. on days 9, 10, 13, 14, and 15 with 200 ul of F127/L61 at 2.25% W:V (8:1 W:W) either once, 2, 3, 4, and 5 times. Time of death (when the rats are paralyzed or paraplegic) or the thickness of the hindpaws was measured with a caliper throughout the experiment and the data are reported below as the increase of thickness over normal rats:

| | F127/L61 at 2.25% W:V (8:1 W:W) | | | | | |
|---|---|---|---|---|---|---|
| Days | (5×) | 1× | 2× | 3× | 4× | 5× |
| 8 | 0 | 0.05 | 0.05 | 0 | 0 | 0 |
| 9 | 1 | 1.05 | 1.2 | 1.4 | 1.3 | 1.583 |
| 10 | 0.95 | 0.75 | 0.85 | 0.7 | 0.85 | 0.93 |
| 13 | 0.7 | 0.95 | 1.3 | 0.85 | 0.6 | 0.97 |
| 15 | 0.01 | 0.35 | 1.45 | 0.9 | 0.1 | 0 |
| 16 | 0.3 | 0.53 | 1.14 | 0.9 | 0.05 | 0 |
| 17 | 0.95 | T | TTT | 1 | 0.35 | 0.47 |
| 20 | 0.95 |  |  | 1.75 | 0.2 | 0 |

-continued

| | F127/L61 at 2.25% W:V (8:1 W:W) | | | | | |
|---|---|---|---|---|---|---|
| Days | (5×) | 1× | 2× | 3× | 4× | 5× |
| 22 | 1.3 |  |  | 2.15 | 0.3 | 0.55 |
| 24 | 0.85 |  |  | 2.1 | 0.15 | 0.33 |
| 25 | TT |  |  | 2.1 | 0.15 | 0.5 |
| 26 |  |  |  | TT | 0 | 0 |

T = day of death/sacrifice

EXAMPLE 12

F127/L61 at 2.25% W:V (8:1 W:W) as an Immunomodulator in Disease Conditions

F127/L61 at 2.25% W:V (8:1 W:W) is considered as an immunomodulator in pathological conditions such as rheumatoid arthritis and inflammation but not in normal physiological conditions. This can be seen from the fact that mice immunized with collagen type II (used to trigger the development symptoms of rheumatoid arthritis) produces titers of specific antibodies against collagen which are reduced following the treatment with F127/L61 at 2.25% W:V (8:1 W:W) (see Example 2). When the same experiments were repeated on non-pathogenic antigenic determinant like β-galactosidase, no such reduction of specific antibodies was observed, suggesting that F127/L61 at 2.25% W:V (8:1 W:W) does not have an inhibitory effect in healthy animals immunized with an antigen that does not lead to the development of a pathology. This observation again reemphasized the fact that F127/L61 at 2.25% W:V (8:1 W:W) exerts it effect only when the immune system is compromised to disease development.

EXAMPLE 13

Toxicity of F127/L61 at 2.25% W:V (8:1 W:W)

The consequence of administering of F127/L61 at 2.25% W:V (8:1 W:W) in normal healthy animals was assessed carefully by means of an analysis of blood chemistry and lymphocytic population. The experiments consisted in injection of F127/L61 at 2.25% W:V (8:1 W:W) in normal mice and numbering various lymphocytic populations like CD4+, CD8+ and B lymphocytes and lymphocyte-activated killer cells as well as their corresponding activities. Despite a short-term discoloration of blood that there was no effect on the number of the different cell populations and on their corresponding activities. Furthermore, F127/L61 at 2.25% W:V (8:1 W:W) was used at a lower concentration in a different application {F127/L61 at 2.25% W:V (8:1 W:W)+ doxorubicin} and was found to be inert in patients.

From the foregoing description, various modifications and changes in the compositions and methods of this invention will occur to those skilled in the art. All such modifications coming within the scope of the appended claims are intended to be included therein.

What is claimed is:
1. A method for reducing inflammation, auto-immune response, and rejection of graft/implantation comprising administering an effective amount of at least one non-ionic block copolymer of the formula

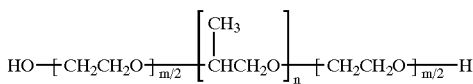

selected from the group consisting of F127 and L61
wherein,
F127 has a molecular weight of 12600, an average number of oxypropylene units (n) of 65.2, an average number of oxyethylene units (m) of 200.4, and a hydrophilic-lipophilic balance of 22; and
L61 has a molecular weight of 2000, an average number of oxypropylene units (n) of 31.0, an average number of oxyethylene units (m) of 4.5, and a hydrophilic-lipophilic balance of 3.

2. The method of claim 1 comprising administering non-ionic block copolymers F127 and L61.

3. A composition for reducing inflammation, auto-immune response, and rejection of graft/implantation consisting essentially of non-ionic block copolymer F127 and non-ionic block copolymer L61 of the formula

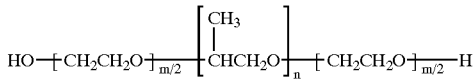

wherein F127 has a molecular weight of 12600, an average number of oxypropylene units (n) of 65.2, an average number of oxyethylene units (m) of 200.4, and a hydrophilic-lipophilic balance of 22;
L61 has a molecular weight of 2000, an average number of oxypropylene units (n) of 31.0, an average number of oxyethylene units (m) of 4.5, and a hydrophilic-lipophilic balance of 3; and
wherein the amount of the non-ionic block copolymer F127 is at least twice the amount of the non-ionic block copolymer L61.

4. The composition of claim 3 wherein the non-ionic block copolymers F127 and L61 are present in the ratio of 8 to 1.

5. The composition of claim 3 wherein the non-ionic block copolymers F127 and L61 are present in the amounts below about 12%.

6. The method of claim 1 wherein the non-ionic block copolymer has critical micellar concentration below about 0.5%.

7. The method of claim 6 wherein the non-ionic block copolymer has critical micellar concentration below about 0.1%.

8. A method for reducing inflammation comprising the step of administering a composition comprising at least one non-ionic block copolymer of the formula

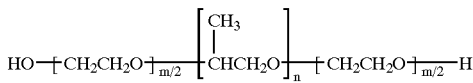

selected from the group consisting of F127 and L61
wherein,
F127 has a molecular weight of 12600, an average number of oxypropylene units (n) of 65.2, an average number of oxyethylene units (m) of 200.4, and a hydrophilic-lipophilic balance of 22; and
L61 has a molecular weight of 2000, an average number of oxypropylene units (n) of 31.0, an average number of oxyethylene units (m) of 4.5, and a hydrophilic-lipophilic balance of 3.

9. The method of claim 8 wherein the composition comprises non-ionic block copolymers F127 and L61.

10. A method for reducing auto-immune response in an animal comprising the step of administering a composition comprising at least one non-ionic block copolymer of the formula

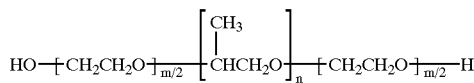

selected from the group consisting of F127 and L61
wherein,
F127 has a molecular weight of 12600, an average number of oxypropylene units (n) of 65.2, an average number of oxyethylene units (m) of 200.4, and a hydrophilic-lipophilic balance of 22; and
L61 has a molecular weight of 2000, an average number of oxypropylene units (n) of 31.0, an average number of oxyethylene units (in) of 4.5, and a hydrophilic-lipophilic balance of 3.

11. The method of claim 10, wherein the composition comprises non-ionic block copolymers F127 and L61.

12. A method for reducing graft/implantation rejection comprising the step of administering a composition comprising at least one non-ionic block copolymer.

13. The method of claim 12, wherein the non-ionic block copolymer of the formula

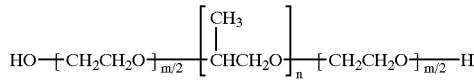

selected from the group consisting of F127 and L61
wherein,
F127 has a molecular weight of 12600, an average number of oxypropylene units (n) of 65.2, an average number of oxyethylene units (m) of 200.4, and a hydrophilic-lipophilic balance of 22; and
L61 has a molecular weight of 2000, an average number of oxypropylene units (n) of 31.0, an average number of oxyethylene units (m) of 4.5, and a hydrophilic-lipophilic balance of 3.

14. A method for treating an animal having rheumatoid arthritis, an inflammatory disease, or an auto-immune disease comprising the step of administering to the in a composition comprising at least one non-ionic block copolymer of the formula

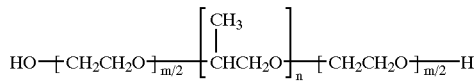

selected from the group consisting of F127 and L61
wherein,
F127 has a molecular weight of 12600, an average number of oxypropylene units (n) of 65.2, an average number of oxyethylene units (m) of 200.4, and a hydrophilic-lipophilic balance of 22; and L61 has a molecular weight of 2000, an average number of oxypropylene units (n) of 31.0, an average number of oxyethylene units (m) of 4.5, and a hydrophilic-lipophilic balance of 3.

15. A composition according to claim 3 wherein the amount of the non-ionic block copolymer F127 is at least four times the amount of the non-ionic block copolymer L61.

* * * * *